United States Patent
Luo et al.

(10) Patent No.: US 11,643,373 B1
(45) Date of Patent: May 9, 2023

(54) INTEGRATED REACTOR FOR IONIC LIQUID ALKYLATION USING BIO-ETHYLENE FEEDSTOCK

(71) Applicant: CHEVRON U.S.A. INC., San Ramon, CA (US)

(72) Inventors: Huping Luo, Moraga, CA (US); Hye-Kyung Cho Timken, Albany, CA (US); Bong-Kyu Chang, Albany, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 0 days.

(21) Appl. No.: 17/954,438

(22) Filed: Sep. 28, 2022

Related U.S. Application Data

(60) Provisional application No. 63/289,697, filed on Dec. 15, 2021.

(51) Int. Cl.
| | | |
|---|---|---|
| *C07C 2/60* | (2006.01) | |
| *B01J 31/02* | (2006.01) | |
| *C07C 2/58* | (2006.01) | |
| *C07C 2/62* | (2006.01) | |

(52) U.S. Cl.
CPC ............ *C07C 2/60* (2013.01); *B01J 31/0277* (2013.01); *B01J 31/0284* (2013.01); *C07C 2/58* (2013.01); *C07C 2/62* (2013.01); *C07C 2531/02* (2013.01)

(58) Field of Classification Search
CPC .... C07C 2/60; C07C 2/58; C07C 2/62; C07C 2531/02; B01J 31/0277; B01J 31/0284
See application file for complete search history.

(56) References Cited

U.S. PATENT DOCUMENTS

| | | | |
|---|---|---|---|
| 3,800,001 A | 3/1974 | Prescott et al. | |
| 3,873,635 A | 3/1975 | Prescott et al. | |
| 7,432,409 B2 | 10/2008 | Elomari et al. | |
| 9,079,815 B2 | 7/2015 | Mukherjee et al. | |
| 2006/0131209 A1* | 6/2006 | Timken | C10L 1/06 208/16 |
| 2006/0135839 A1* | 6/2006 | Elomari | C10G 29/205 585/709 |
| 2009/0171133 A1 | 7/2009 | Luo et al. | |
| 2009/0171134 A1* | 7/2009 | Luo | B01J 4/002 585/14 |
| 2011/0308146 A1* | 12/2011 | O'Rear | C07C 2/60 585/16 |
| 2012/0051953 A1* | 3/2012 | O'Rear | C07C 1/20 585/311 |
| 2012/0053378 A1* | 3/2012 | O'Rear | C07C 1/20 585/302 |
| 2012/0238787 A1* | 9/2012 | Gruber | C12P 5/00 585/16 |
| 2013/0011893 A1* | 1/2013 | Mantegazza | C07C 2/864 585/323 |

(Continued)

OTHER PUBLICATIONS

J-M. Goupil, J-L. Poirier and D. Cornet "Alkylation of Isobutane by Ethylene: A Thermodynamic Study" Ind. Eng. Chem. Res. 1994, 33, 712-717.

*Primary Examiner* — Ali Z Fadhel

(57) ABSTRACT

An alkylation process is described. The process involves alkylation of isobutane and ethylene in a loop reactor using an ionic liquid catalyst as a continuous phase. The alkylate typically has a research octane number of at least about 93, and the olefin conversion is typically at least about 95%.

15 Claims, 3 Drawing Sheets

(56) References Cited

U.S. PATENT DOCUMENTS

| | | | |
|---|---|---|---|
| 2016/0194257 A1* | 7/2016 | Lilga | B01J 23/42 |
| | | | 585/517 |
| 2020/0062674 A1* | 2/2020 | Cao | C10G 69/06 |
| 2021/0040012 A1* | 2/2021 | Richardson | C07C 2/08 |
| 2022/0106529 A1* | 4/2022 | Kapelewski | B01J 29/708 |
| 2022/0204663 A1* | 6/2022 | Kasireddy | C07C 41/16 |
| 2023/0027277 A1* | 1/2023 | Kapelewski | B01J 29/90 |

\* cited by examiner

INTEGRATED REACTOR FOR IONIC LIQUID ALKYLATION USING BIO-ETHYLENE FEEDSTOCK

CROSS-REFERENCE OF RELATED APPLICATIONS

This application claims the priority benefit of U.S. Provisional Patent Application No. 63/289,697, filed Dec. 15, 2021, the disclosure of which is incorporated herein by reference.

FIELD

This present disclosure relates alkylation processes using an ionic liquid as a catalyst, and more particularly, to alkylation processes that use ethylene feedstocks, and even more specifically, to alkylation processes that utilize nozzle loop reactors.

BACKGROUND

Because of its clean-fuel properties (e.g., high octane rating, low-vapor pressure, and low sulfur content), alkylate is considered one of the most desired components in the gasoline pool. As demand for cleaner-burning fuel has increased, refiners are relying more than ever on alkylate to meet stringent gasoline specifications. With increasing pressure to reduce motor vehicle exhaust emissions, alkylate is well-positioned to be in steady demand for decades to come.

Most alkylate is produced in refineries by a process known as isoparaffin alkylation. Commercially, isoparaffin alkylation is an acid catalyzed reaction that combines C3-C5 light olefins from a fluid catalytic cracking (FCC) unit with isobutane to produce a relatively high octane branched-chain paraffinic hydrocarbon fuel, including iso-heptane and iso-octane. Predominant alkylation technologies utilized by refiners require a liquid acid catalyst such as sulfuric acid ($H_2SO_4$) or hydrofluoric acid (HF).

Ethylene is another major component produced in the FCC unit. However, the direct alkylation of ethylene has not been possible with conventional liquid acid alkylation catalysts (e.g., $H_2SO_4$, HF) and processes due to the relatively slow kinetics of the reaction. Efforts to produce alkylate from ethylene have relied on dimerizing ethylene to butylene in a dimerization process unit, followed by alkylation with isobutane in the alkylation process unit. This method requires significant extra capital investment for the dimerization unit. In addition, alkylate yield per barrel of ethylene is very low.

Therefore, there is a need for an improved process for alkylation of light olefins.

SUMMARY

In one aspect, there is provided a process for the catalytic alkylation of an olefin with an isoparaffin in a loop reactor system, the process comprising: (a) introducing an ethylene feed and an isobutane feed into a loop reactor system comprising at least one loop reactor; (b) supplying an ionic liquid catalyst to the reactor system, wherein the ionic liquid catalyst comprises an organic cation and a halometallate anion, and the ionic liquid is present in an amount of at least 35 vol. % of a total volume of fluid in the loop reactor system; and (c) circulating the ethylene feed and isobutane feed through the loop reactor in the presence of the ionic liquid catalyst under reaction conditions effective for reaction between the ethylene and the isobutane to produce an alkylate having a research octane number (RON) of 93 or more; wherein the reaction conditions include a temperature of from 30° C. to 100° C., a pressure of from 300 psig to 700 psig (2068 kPa to 4826 kPa), and an overall paraffin to olefin molar ratio of from 2 to 20.

DETAILED DESCRIPTION

Definitions

Figure 1:
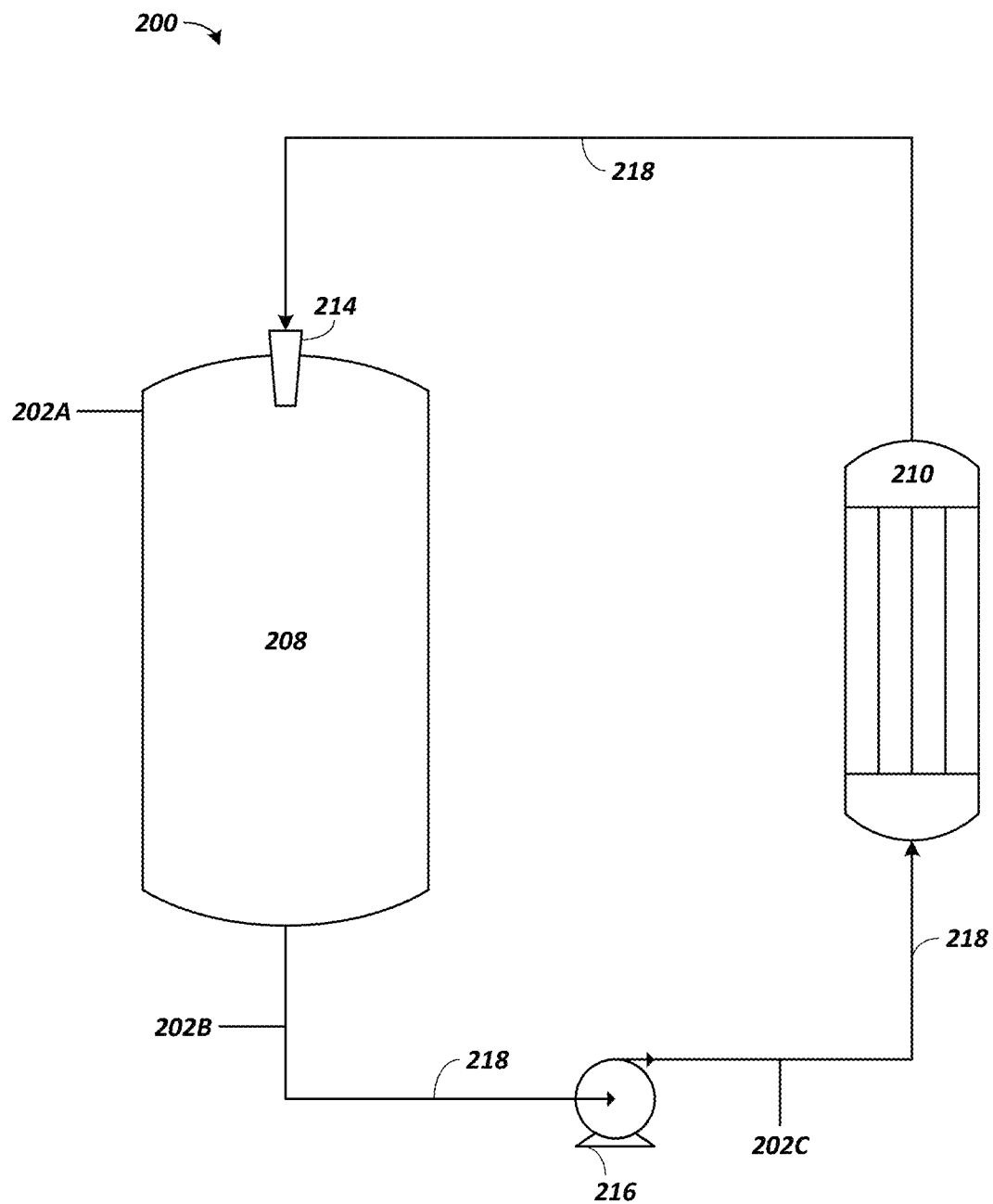
FIG. 1 is a schematic diagram of an exemplary alkylation system and process.

The term "alkylate" means the reaction products generated in alkylation reactions between an olefin and an isoparaffin in the presence of a catalyst. Alkylates typically are highly branched paraffinic hydrocarbons. Refiners can use alkylate as a gasoline blend stock to boost octane, reduce Reid vapor pressure (RVP), and reduce olefin content in a final gasoline blend.

The term "Cn hydrocarbons" or "Cn", wherein "n" is a positive integer, means hydrocarbons having "n" number of carbon atoms. The term "Cn+" is meant to describe a mixture of hydrocarbons having "n" or more carbon atoms. The term "Cn-" is meant to describe to a mixture of hydrocarbons having "n" or less carbon atoms.

"Ethylene" may be abbreviated as "C2=".

"Isobutane" may be abbreviated as "i-C4".

The term "octane number" refers to the percentage of iso-octane in a mixture of iso-octane and n-heptane that would have the same knock resistance as the presently tested fuel, according to ASTM D2699 and D2700. Octane numbers typically range from 0 to 100, with higher values indicating better fuel performance. Octane numbers are unitless.

The term "Research Octane Number" (RON) refers to the octane number obtained by testing at lower engine speed and temperature, typically about 600 rpm, according to ASTM D2699.

The term "loop reactor" does not denote a certain design, but only the principle of operation. In the most simple case, the loop reactor consists of a circularly closed tube (loop) equipped with a circulating pump. The loop has at least one connection for withdrawing a product stream and at least two connections for feeding the starting materials.

The term "continuous phase" refers to a liquid phase in which the reaction components (i.e., isobutane, ethylene, co-catalyst, etc.) are dissolved, suspended and/or emulsified.

The term "fluid" includes one or more liquids, one or more gases, or a combination thereof. Different liquids or gases within a fluid may be miscible or immiscible.

The terms "wt. %", "vol. %", or "mol. %" refers to a weight, volume, or molar percentage of a component, respectively, based on the total weight, the total volume of material, or total moles, that includes the component. In a non-limiting example, 10 grams of component in 100 grams of the material is 10 wt. % of component.

Isobutane Feed

The isobutane feed stream to alkylation unit generally comprises at least 50 wt. % isobutane (e.g., 50 wt. % to 99 wt. % isobutane, or 50 wt. % to 95 wt. % isobutane, or 55 wt. % to 90 wt. % isobutane, or at least 80 wt. % isobutane, or 80 wt. % to 98 wt. % isobutane, or 90 wt. % to 97 wt. % isobutane), with at least 90 wt. % (e.g., at least 99 wt. %) of the remainder comprising n-butane. The isobutane feed may be substantially free of one or more of (i) butenes, including isobutene, (ii) C5+ hydrocarbon, and (iii) C3-hydrocarbon. In this context, the term "substantially free" means the isobutane feed comprises less than or equal to 1.0 wt. % of the designated compounds (e.g., less than or equal to 0.1 wt. %, or less than or equal to 0.01 wt. %, or less than or equal to 0.001 wt. %).

Ethylene Feed Stream

Ethylene feed streams useful herein may include dilute ethylene streams, containing up to 50 wt. % ethylene, for example. In some aspects, the ethylene feed stream may include a low purity ethylene feed, including 60 wt. % to 95 wt. % ethylene. In other aspects, the ethylene feed stream may include high purity ethylene (95 wt. % to 99+ wt. % ethylene).

The dilute ethylene stream derived from any number of refinery streams. The dilute ethylene stream may be an off-gas from a refinery unit selected from an ethylene cracker, a fluid catalytic cracker, a coker, a naphtha cracker, a Fischer-Tropsch synthesis unit, an ethylene polymerization unit, or a pyrolysis unit.

The dilute ethylene stream may contain from 0.1 wt. % to 50 wt. % ethylene, such as from 5 wt. %, 10 wt. %, or 15 wt. % to 30 wt. %, 40 wt. %, or 50 wt. % ethylene. A suitable dilute ethylene stream may comprise from 5 wt. % to 50 wt. % ethylene. The balance of the dilute ethylene stream may include hydrogen, methane, ethane, propylene, and/or propane. For example, a typical FCC off-gas may include 50 wt. % to 70 wt. % methane and hydrogen, with the balance being about equal parts ethane and ethylene, as well as a minor amount of C3+ compounds.

In some aspects, the ethylene feed stream may be a polymer-grade ethylene stream, which may have at least 98 wt. %, or at least 99 wt. %, or at least 99.5 wt. %, or at least 99.8 wt. % ethylene.

Ethylene can be derived from petroleum resources or from renewable/sustainable sources. Bio-based ethylene can be produced by dehydration of ethanol obtained through fermentation or other microbial production processes.

Ionic Liquid

The ionic liquid comprises an organic cation and an anion. The organic cation is generally a nitrogen-based cation, a phosphorus-based cation, or a combination thereof. Representative organic cations include ammonium, pyrrolidinium, pyridinium, imidazolium, and phosphonium cations.

Examples of ammonium cations include tetraalkylammonium cations, such as tri(C1-C6 alkyl)-(C2-C10 alkyl)ammonium cations. Representative ammonium cations include trimethyl-n-propylammonium, n-butyl-trimethylammonium, n-hexyl-trimethylammonium, triethyl-methylammonium, tetraethylammonium, n-butyl-triethylammonium, and tetra-n-butylammonium.

Examples of pyrrolidinium cations include N-alkylpyrrolidinium cations, such as N-(C2-C6alkyl)pyrrolidinium cations, and N,N-dialkylpyrrolidinium cations, such as N-(C1-C3 alkyl)-N-(C2-C6 alkyl)pyrrolidinium cations. Representative pyrrolidinium cations include N-propylpyrrolidinium, N-butylpyrrolidinium, N-methyl-N-propylpyrrolidinium and N-butyl-N-methylpyrrolidinium.

Examples of imidazolium cations include 1,3-dialkylimidazolium cations, such as 1-(C2-C10 alkyl)-3-(C1-C3alkyl) imidazolium cations. Representative imidazolium cations include 1-ethyl-3-methylimidazolium, 1-n-butyl-3-methylimidazolium, 1-n-hexyl-3-methylimidazolium, and 1-n-octyl-3-methylimidazolium.

Examples of pyridinium cations include N-alkylpyridinium cations, such as N-(C2-C6 alkyl)pyridinium cations, and N-alkyl-alkylpyridinium cations, such as N-(C2-C6alkyl)-(C1-C3 alkyl)pyridinium cations. Representative pyridinium cations include N-ethylpyridinium, N-butylpyridinium, N-propyl-4-methylpyridinium and N-butyl-4-methylpyridinium.

Examples of phosphonium cations include tetraalkylphosphonium cations, such as tri(C1-C10 alkyl)-(C2-C20 alkyl) phosphonium cations. Representative phosphonium cations include triethyl-pentylphosphonium, tetrabutylphosphonium, and trihexyl-tetradecylphosphonium.

The anion of the ionic liquid comprises a halometallate. Halometallate anions may contain a metal selected from Al, Ga, In, Mn, Fe, Co, Ni, Cu, Zn, or combinations thereof, and a halide selected from F, Cl, Br, I, or combinations thereof. In some aspects, the anion of the ionic liquid comprises a haloaluminate. In some aspects, the anion of the ionic liquid comprises a chloroaluminate. For catalytic applications requiring Lewis acidity (such as alkylation), the ratio of moles of halide to moles of metal in the halometallate anion is less than 4. The anion may be formally an anion or it may be an anion associated with a metal halide. For instance, the anion may be $AlCl_4^-$ or $Al_2Cl_7^-$ associated with $AlCl_3$. In some aspects, the anion may be $GaCl_4^-$ or $Ga_2Cl_7^-$ or $Ga_3Cl_{10}^-$ associated with $GaCl_3$ The ionic liquid catalyst can include a co-catalyst (or catalyst promoter) to enhance the activity of the ionic liquid catalyst by boosting its overall acidity. The co-catalyst may be a Brønsted acid and/or a Brønsted acid precursor. The co-catalyst is present in an amount of 0.05 mol to 1 mol of co-catalyst per mol of ionic liquid, or 0.05 mol to 0.7 mol, or 0.05 mol to about 0.5 mol, or 0.1 mol to 0.7 mol, or 0.1 mol to 0.5 mol. Suitable Brønsted acids include HCl, HBr, HI, and combinations thereof. In some aspects, the co-catalyst can be generated in situ from appropriate Brønsted acid precursors. Suitable Brønsted acid precursors include chloroalkanes such as 1-chloropropane, 2-chloropropane, 1-chlorobutane, 2-chlorobutane, 1-chloro-2-methylpropane, 2-chloro-2-methylpropane, and other chloroalkanes, preferably secondary or tertiary chloroalkanes, or combinations thereof. In some aspects, the Brønsted acid precursor is a chloroalkane having more than one chloride atom per molecule such as dichloromethane, chloroform, carbon tetrachloride, tetrachloroethylene, tetrachloropropene, or combinations thereof.

Alkylation

In conventional alkylation processes using an ionic liquid catalyst, due to relatively high catalyst activity, a small amount of acid catalyst is used (e.g., 5-10 vol %). As a result, the hydrocarbon reactants (i.e., isoparaffin and C3-C5 olefins) form a continuous phase in the alkylation reactor while the ionic liquid catalyst forms a dispersed phase or small droplets suspended in the hydrocarbon phase. This liquid-liquid dispersion requires highly intimate contact between the ionic liquid and the hydrocarbon phases.

Although ionic liquid catalysts are quite effective in alkylating C3-C5 olefins, they are not effective in activating ethylene at low catalyst volumes. The alkylation process of present disclosure therefore uses a relatively large amount of ionic liquid catalyst in the system (e.g., at least 35 vol %). As a result, the ionic liquid forms a continuous phase in the reactor while the hydrocarbons form a dispersed phase or small droplets suspended in the ionic liquid phase.

The alkylation process according to the present disclosure is carried out with particular advantage in a loop reactor with a reaction chamber and a heat exchanger, wherein the reaction chamber and the heat exchanger are in fluid communication with each other via at least one conduit such that a fluid in the reaction chamber can be circulated through the heat exchanger and returned to the reaction chamber. The process introduces, not necessarily at the same time, an isobutane feed, an ethylene feed, and an ionic liquid catalyst into the loop reactor. The loop rector can provide sufficient mixing between the hydrocarbon reactants and ionic liquid catalyst under conditions favorable for ethylene alkylation.

An exemplary loop reactor 200 that may be used in alkylation processes of the present disclosure is shown in FIG. 1. Referring to FIG. 1, loop reactor 200 comprises reaction chamber 208, heat exchanger 210, conduit 218, lines 202A, 202B, and 202C, pump 216, nozzle 214, and pump 216.

Ionic liquid catalyst is supplied to the reactor 200 via line 202A. Ethylene and isobutane are supplied into the nozzle 214, which is provided at the top portion of the reactor chamber 208 and mixed with circulating ionic liquid catalyst. The ethylene and isobutane, which had been sprayed into the reaction chamber 208, undergo alkylation in the presence of the ionic liquid catalyst to generate the reaction mixture. The biphasic reaction mixture contains a hydrocarbon phase (e.g., alkylate) and an ionic liquid phase.

Reaction chamber 208 and heat exchanger 210 are in fluid communication with one another through conduit 218 such that fluids in reaction chamber 208 can be circulated through heat exchanger 210 and returned to reaction chamber 208.

Along conduit 218 may exist various lines that serve as entry points or exit points for loop reactor 200. FIG. 1 includes lines 202B and 202C between reaction chamber 208 and heat exchanger 210. Ionic liquid catalyst is added to the reactor 200 via line 202B. Reaction effluent is diverted from the reactor 200 through line 202C, and from there the reaction effluent is passed to a recovery equipment (not shown) to isolate the desired alkylate by methods known per se. The remainder of the reaction effluent circulates through the loop reactor 200.

Heat exchanger 210 can be any device used to transfer heat. The heat exchanger 210 may be a standard shell-and-tube heat exchanger in which brine water passes through the shell of the heat exchanger 210 for cooling or heating the reactor effluent which flows through the tube portion of the heat exchanger 210.

Pump 216 serves to provide a means for circulating the reactor contents in loop reactor 200. In doing so, pump 216 helps regulate the temperature of the system by circulating the reactor contents to pass through heat exchanger 210. Pump 216 may also increase mixing by increasing the turnover rate in loop reactor 200. Pump 216 may be any pump suitable for the recycling rate and the flow required.

It will be appreciated that present alkylation process may utilize additional loop reactors or other reactors (e.g., liquid-phase reactors) which may be arranged in series or parallel.

Typical alkylation reaction conditions include a minimum temperature of 30° C., or 35° C., or 40° C., or 45° C., or 50° C., or 55° C., or 60° C.; additionally or alternatively, a maximum temperature of 100° C., or 95° C., or 90° C., or 85° C., or 80° C., or 75° C., or 70° C. Generally, the temperature can be in a range from any minimum temperature disclosed herein to any maximum temperature disclosed herein. It is preferred to have the ionic liquid that maintains its liquid state through the operating temperature range.

The alkylation reaction can be conducted at a pressure of from 100 psig to 1000 psig (689 kPa to 6895 kPa), such as 300 psig to 700 psig (2068 kPa to 4826 kPa), or 350 psig to 500 psig (2413 kPa to 3447 kPa). Preferably, the reactants are maintained in a liquid state at the operating pressure.

The residence time of the reactants in the reactor can be in a range of from a few seconds to several hours (e.g., 30 seconds to 1 hour, or 2 minutes to 30 minutes, or 2 minutes to 10 minutes, or 5 minutes to 1 hour, or 5 minutes to 30 minutes, 5 minutes to 10 minutes).

The volume of ionic liquid in the reactor, based on a total volume of fluid in the reactor (ionic liquid and hydrocarbons), can have a minimum value of 35 vol. %, or 40 vol. %, or 45 vol. % or 50 vol. %, based on a total volume of fluid in the reactor (ionic liquid and hydrocarbons); or alternatively, a maximum value of 75 vol. %, or 70 vol. %, or 65 vol. %, or 60 vol. %, or 55 vol. %. Generally, the volume of ionic liquid in the reactor can be in a range from any minimum value disclosed herein to any maximum value disclosed herein.

Due to the low solubility of hydrocarbons in ionic liquids, isoparaffin-olefin alkylation, like most reactions in ionic liquids, is generally biphasic. The catalytic alkylation reaction is generally carried out in a mixed phase liquid-liquid system. The system can be a batch system, a semi-batch system, or a continuous system as is usual for aliphatic alkylation. Vigorous mixing is desirable to ensure good contact between the reactants and the catalyst.

The isoparaffin and olefin can be introduced into the reactor separately or as a mixture, in one or multiple locations. The molar ratio of isoparaffin to olefin is generally 20:1 or less, or 15:1 or less, or 10:1 or less, or in a range of 2:1 to 20:1, or in a range of 2:1 to 15:1, or in a range of 2:1 to 10:1, or in a range of 2:1 to 8:1, or in a range of 2:1 to 6:1, or in a range of 2:1 to 4:1, or in a range of 5:1 to 20:1, or in a range of 5:1 to 15:1, or in a range of 5:1 to 10:1 .

In a semi-batch system, the catalyst, optional co-catalyst, and at least a portion of the isoparaffin are introduced with no olefin present, followed by the olefin or a mixture of isoparaffin and olefin. In a semi-batch system, the olefin is added gradually over a period of time. The catalyst is measured in the reactor with respect to the amount of total olefins added over the course of the reaction, with a catalyst to olefin weight ratio in a range of from 0.1:1 to 10:1 (e.g., 0.2:1 to 5:1, or 0.5:1 to 2.5:1).

In a continuous system, the ionic liquid catalyst, the isoparaffin, the olefin, and optionally the co-catalyst are each added continuously. Catalyst, optional co-catalyst, unreacted isoparaffin, and unreacted olefin are each removed continuously from the reaction zone along with alkylate product. The catalyst, co-catalyst, unreacted isoparaffin, and/or unreacted olefin may be recycled. The olefin may be added to one or more locations in the reaction zone. It is preferable to add the olefin to multiple locations in the reaction zone. Adding olefin in multiple locations or spreading the olefin addition over a longer period of time, results in the isoparaffin to olefin ratio measured in a specific location at a specific point in time to be higher. The isoparaffin to olefin ratio is defined as the cumulative amount of isoparaffin divided by the cumulative amount of olefin added across the entire reaction zone.

Conjunct polymer forms as a by-product of the alkylation reaction. Conjunct polymers are typically highly conjugated, olefinic, highly cyclic hydrocarbons and have a strong affinity for the ionic liquid catalyst. The ionic liquid catalyst loses its effectiveness over time as the amount of conjunct polymer increases. Over time, the ionic liquid catalyst must then either be replaced or regenerated. Generally, only as much ionic liquid catalyst is regenerated as is necessary to maintain a desired level of catalyst activity. Generally, the alkylation process is operated at conditions sufficient to maintain a desired level of conjunct polymer in the ionic liquid. The amount of conjunct polymer in the ionic liquid during alkylation may be maintained at 10 wt. % or less (e.g., 9 wt. % or less, or 8 wt. % or less, or 7 wt. % or less, or 6 wt. % or less, or 5 wt. % or less, or 4 wt. % or less, or 3 wt. % or less, or 2 wt. % or less, 1 wt. % or less). For example, the amount of conjunct polymer in the spent ionic liquid may be maintained in a range of from 0.5 to 10 wt. %, or 1 to 5 wt. %, or 2 to 4 wt. %. An amount of conjunct polymer in an ionic liquid phase can be measured using infrared spectroscopy, such as disclosed in U.S. Pat. No. 9,290,702.

The reactor effluent that is contained in the reactor following the alkylation process, which contains the alkylation product and typically some residual isobutane (along with other components, e.g., conjunct polymer), can be subjected to a separation process to remove some of the more volatile components from the alkylation reactor effluent, to provide a hydrocarbon product.

At a reactor outlet, the reactor effluent contains a hydrocarbon phase and an ionic liquid phase. The hydrocarbon phase is separated from the ionic liquid phase by gravity settling based on density differences, or by other separation techniques known to those skilled in the art. Then the hydrocarbons are separated by distillation, and the starting isoparaffin which has not been converted is recycled to the reactor. The catalyst is typically recycled to the reactor as well.

Typical alkylation conditions may include a temperature of from 30° C. to 100° C., a pressure of from 300 psig to 700 psig (2068 kPa to 4826 kPa), an isoparaffin to olefin molar ratio of from 2:1 to 20:1, and an ionic liquid volume in the reactor of at least 35 vol. %.

The conversion of ethylene is typically at least 95% (e.g., at least 96%, or at least 97%, or at least 98%, or at least 99%). The percent ethylene conversion is defined as: (the amount of ethylene added to the reactor minus the amount of ethylene remaining after the reaction (or at the reactor outlet)) divided by the total amount of ethylene added to the reactor times 100. In a continuous process, ethylene conversion is defined as: (the amount of ethylene added to the reactor minus the total flow of ethylene out of the reactor) divided by the total flow of ethylene into the reactor.

The effluent fluid diverted from the reactor contains alkylate, unreacted isobutane, the ionic liquid catalyst, and possibly unreacted ethylene. The effluent fluid can be sent to a separation zone where it is separated into a hydrocarbon stream comprising the alkylate and unreacted isobutane (and any unreacted ethylene) and an ionic liquid recycle stream. Suitable separation zones include gravity settlers, coalescers, filtration zones comprising sand or carbon, adsorption zones, scrubbing zones, or combinations thereof.

The hydrocarbon stream can be sent to a hydrocarbon separation zone where it is separated into an alkylate stream and an isobutane and co-catalyst recycle stream. The alkylate stream can be recovered and further treated as needed. The isobutane can be recycled to the reactor, if desired. Suitable hydrocarbon separation zones include distillation or vaporization.

The ionic liquid recycle stream which typically contains some amount of conjunct polymer is also recovered from the separation zone and can be recycled to the reactor, if desired. In some embodiments, at least a portion of the ionic liquid recycle stream can be sent to a regeneration zone to remove at least some of the conjunct polymer from the ionic liquid recycle stream to provide a regenerated ionic liquid. The regenerated ionic liquid recycle stream can be recycled to the reactor.

Alkylate

In some aspects, the process can be used to upgrade low value C4 hydrocarbons to higher value alkylates. To that extent, one specific aspect is the alkylation of isobutane with ethylene to generate C6 compounds. Preferred products include isomers of dimethylbutane (DMB), namely, 2,3-dimethylbutane and 2,2-dimethylbutane. Other C6 isomers are also produced. One set competing isomers are methylpentanes (MP), namely 2-methylpentane and 3-methylpentane. The quality of the alkylate can be measured in the ratio of DMB to MP, with a high ratio desired (e.g., at least 7:1 or more, or at least 10:1 or more, or at least 12:1 or more, or at least 15:1 or more, or at least 20:1 or more).

In some aspects, the alkylation reaction can have a selectivity for C6 of at least 65% or more, or at least 70% or more, or at least 75% or more. Selectivity for C6 is defined here as the total weight of products containing exactly six carbon atoms divided by the total weight of products containing five or more carbon atoms. In some aspects, the alkylate can have a mole ratio of dimethylbutane to methylpentane of 4:1 or more, or 7:1 or more, or 10:1 or more, or 15:1 or more, or 20:1 or more, or 25:1 or more, or 30:1 or more, or 35:1 or more.

The alkylate may contain C8 paraffins. Preferred products include isomers of trimethylpentane (TMP), namely 2,2,3-trimethylpentane, 2,2,4-trimethylpentane, 2,3,3-trimethylpentane, and 2,3,4-trimethylpentane. Other C8 isomers are also produced. One set of competing isomers are dimethylhexanes (DMH), namely 2,2-dimethylhexane, 2,3-dimethylhexane, 2,4-dimethylhexane, 2,5-dimethylhexane, 3,3-dimethylhexane, and 3,4-dimethylhexane. The quality of the product stream can be measured in the ratio of total TMP to total DMH, with a higher ratio desired (e.g., of greater than 2:1, or greater than 3:1). C8 isomers may be present in an amount of 30 wt. % or less (e.g., 1 wt. % to 30 wt. %, or 5 wt. % to 15 wt. %) of the alkylate.

The alkylate may contain C9+ paraffins. The C9+ paraffins may be present in an amount of less than 20 wt. % (e.g., less than 10 wt. %) of the alkylate.

In some embodiments, the alkylate has a research octane number (RON) of 93 or more (e.g., 94 or more, 95 or more, 96 or more, 97 or more, 98 or more, 99, or 100 or more).

EXAMPLES

The following illustrative examples are intended to be non-limiting.

Example 1

Isobutane-ethylene alkylation was carried out in a 1-liter autoclave reactor. Isobutane and ethylene feeds were combined and fed into the reactor via a dip tube in the vicinity of an impeller. Ionic liquid catalyst (N-butylpyridinium chloroaluminate) was fed via another inlet to the reactor. Reactor effluent was withdrawn from the top of the reactor.

The reactor was operated at 60° C. (140° F.) and 1.22 MPa (180 psig). The feed rates of the reactants were as follows: 2500 cm$^3$/h for isobutane, 900 sccm (standard cubic centimeters per minute) for ethylene, and 300 cm$^3$/h for the ionic liquid catalyst. Alkylation reactions were run at two different agitation rates: 1000 rpm and 1750 rpm. The results are presented in Table 1.

TABLE 1

Conditions and Results for Isobutane Alkylation with Ethylene

|  | Run A | Run B |
|---|---|---|
| Alkylation Conditions | | |
| Continuous Phase | Ionic Liquid | Hydrocarbon |
| Temperature [° C.] | 60 | 60 |
| Pressure [MPa] | 1.22 | 1.22 |
| Agitation Rate [rpm] | 1000 | 1750 |
| Ionic Liquid Content [vol. %] | 43.7 | 13.5 |
| Ethylene Conversion [%] | 97 | 57.5 |
| C5+ Alkylate Composition | | |
| C5 | 2.6 | 2.1 |
| C6 | 76.5 | 50.5 |
| C7 | 2.2 | 4.3 |
| C8 | 14.9 | 32.9 |
| C9 | 1.4 | 1.9 |
| C10 | 1.7 | 4.6 |
| C11 | 0.5 | 3.1 |
| C12+ | 0.1 | 0.6 |
| C6 Isomer Relative Distribution [%] | | |
| 2,3-Dimethylbutane | 97.0 | 97.0 |
| Methylpentanes | 2.8 | 3.0 |
| n-Hexane | 0.0 | 0.0 |
| Other C6 | 0.2 | 0.0 |
| C8 Isomer Relative Distribution [%] | | |
| Trimethylpentanes | 65.4 | 20.3 |
| Dimethylhexanes | 32.9 | 75.6 |
| Methylheptanes | 1.7 | 3.5 |
| n-Octane | 0.0 | 0.0 |
| Other C8 | 0.0 | 0.6 |
| Octane Number | | |
| RON | 100 | 98.1 |
| SIMDIST (ASTM D2887) [° F.] | | |
| Final Boiling Point | 317 | 415 |

For Run A, where more ionic liquid catalyst was in the reactor, high conversion of ethylene was observed, as expected.

For both Run A and Run B, the predominant C6 product was 2,3-dimethylbutane (RON=103.5).

However, the C8 product distributions for Run A and Run B were quite different. For Run A, where a low agitation rate was used and the ionic liquid catalyst volume in the reactor was high, the predominant C8 product was a mixture of trimethylpentanes (RON=100-110). For Run A, where a high agitation rate was used and the ionic liquid catalyst volume in the reactor was low, the predominant C8 product was a mixture of dimethylhexanes (RON=56-76).

Without intending to be bound by a particular theory, it is believed that the mechanism for C8 formation is related to the catalyst volume in the reactor. It is believed that formation of C8 paraffins in Run B (catalyst content=13.5 vol. %) proceeds via a two-step mechanism whereby alkylation of isobutane with ethylene first produces a C6 carbonium ion intermediate, which subsequently reacts with another ethylene molecule to produce C8 alkylate, predominantly dimethylhexanes. It is believed that in Run A (catalyst content=43.5 vol. %) two moles of ethylene initially react to form a tert-butyl C4 carbonium intermediate which subsequently reacts with isobutane to produce C8 alkylate, predominantly trimethylpentanes.

The results suggest that reactor design is an important factor in producing high octane alkylate.

Example 2

Figure 2:
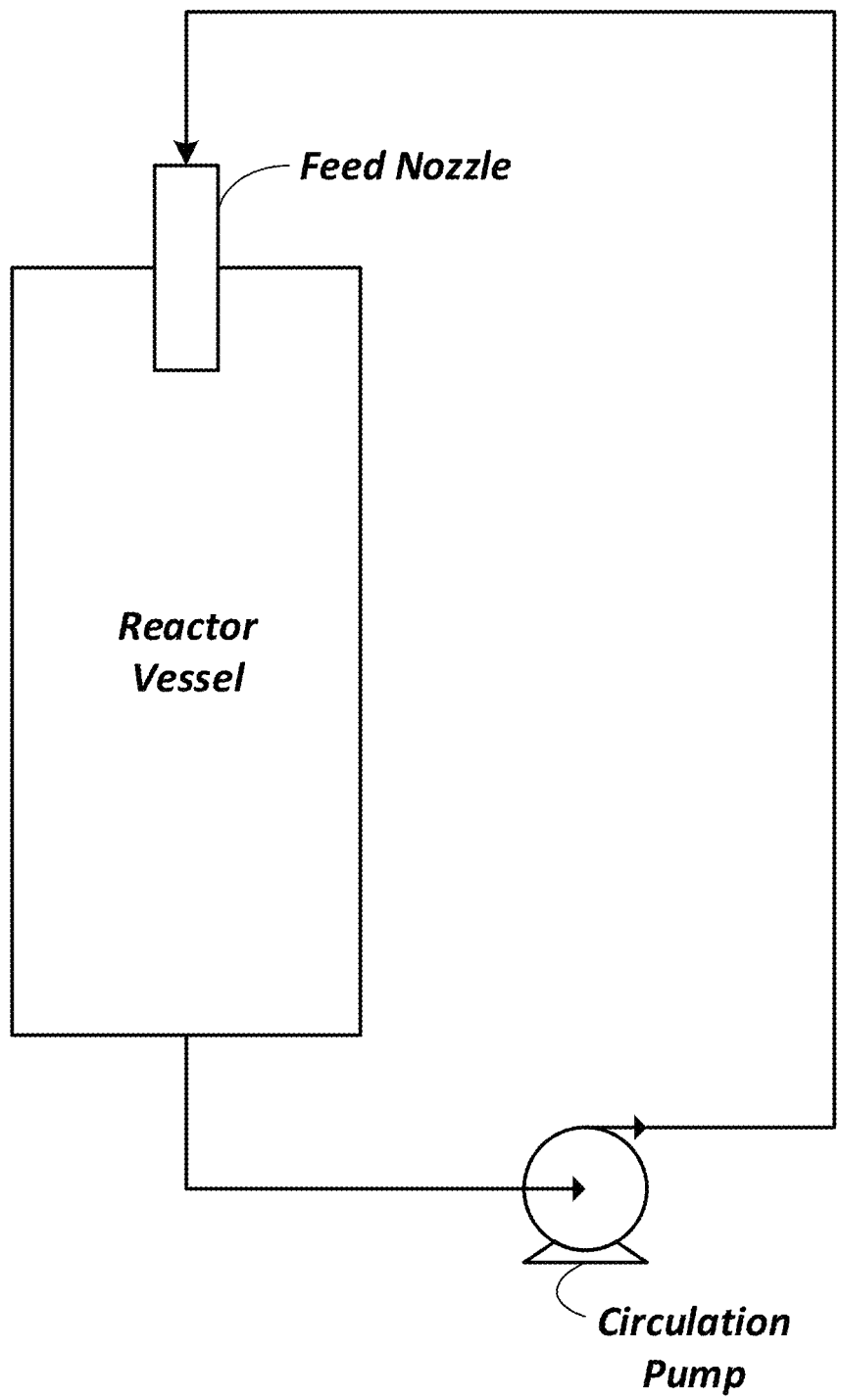
FIG. 2 is a schematic diagram of a cold flow testing unit used in Example 2.

A cold flow testing unit, consisting of a reactor vessel, a feed nozzle and a circulation pump as shown in FIG. 2, was filled with a mixture of ionic liquid (N-butylpyridinium chloroaluminate) and n-heptane before circulating the mixture around the entire system at a certain pump speed. A Coriolis flow meter was used to measure the pump flow rate and the mixture density. The pressure drop across the feed nozzle was also monitored. For a mixture of certain concentration of ionic liquid, several pump speeds were tested. When the system reached a steady state, a small sample was taken from the reactor vessel effluent to determine which phase was the continuous phase.

Figure 3:
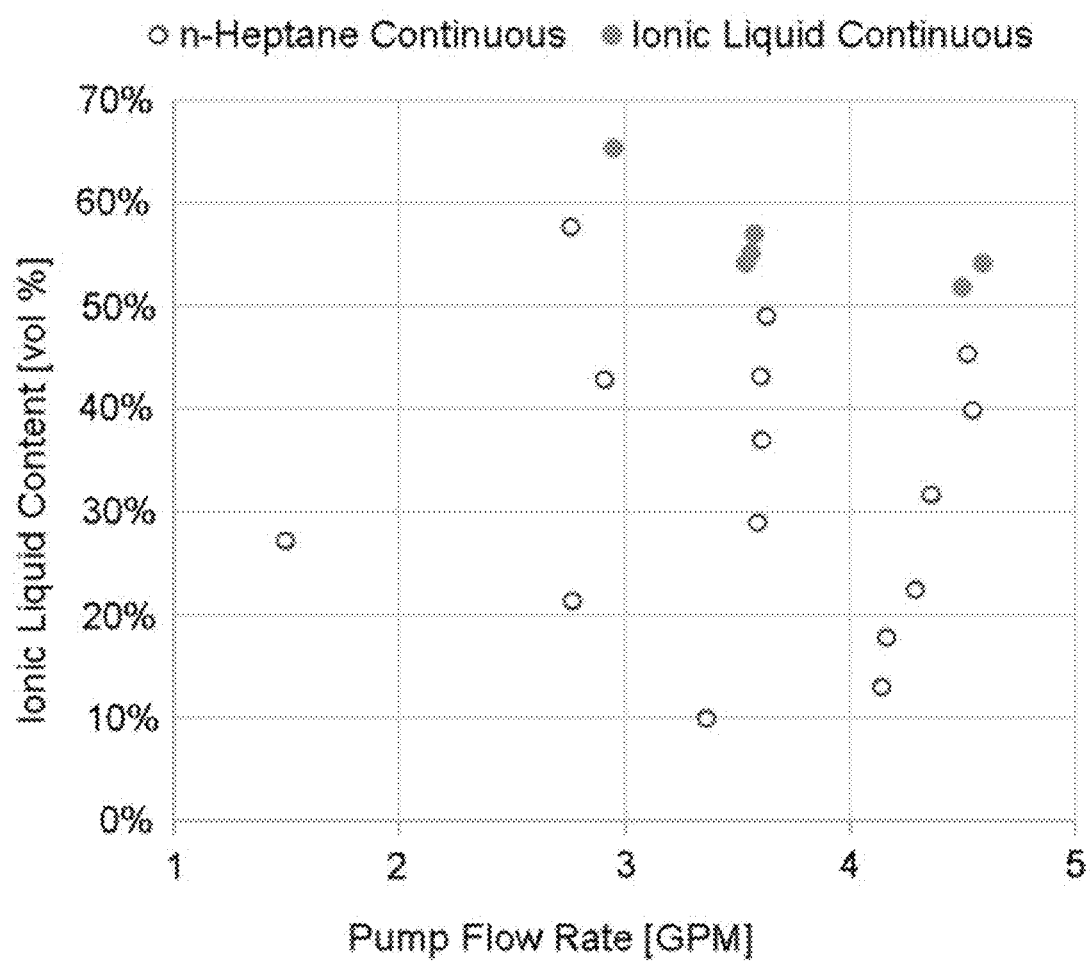
FIG. 3 is a plot of ionic liquid content versus pump flow rate for Example 2.

FIG. 3 shows the results at a combination of different circulation flow rates and ionic liquid concentrations. As can be seen, n-heptane was likely the continuous phase at relatively low pump speeds and at an ionic liquid concentration lower than 50 vol. %. To make the ionic liquid the continuous phase, an ionic liquid concentration of greater than 50 vol. % was required under the tested conditions.

The invention claimed is:

1. A process for the catalytic alkylation of an olefin with an isoparaffin in a loop reactor system, the process comprising:
    (a) introducing a bio-ethylene feed and an isobutane feed into a loop reactor system comprising at least one loop reactor;
    (b) supplying an ionic liquid catalyst to the reactor system, wherein the ionic liquid catalyst comprises an organic cation and a halometallate anion, and the ionic liquid is present in an amount of at least 35 vol. % of a total volume of fluid in the loop reactor system;
    (c) circulating the ethylene feed and isobutane feed through the loop reactor in the presence of the ionic liquid catalyst under reaction conditions effective for reaction between the ethylene and the isobutane to produce an alkylate having a research octane number (RON) of 93 or more;
    wherein the reaction conditions include a temperature of from 30° C. to 100° C., a pressure of from 300 psig to 700 psig (2068 kPa to 4826 kPa), and an overall paraffin to olefin molar ratio of from 2 to 20; and
    wherein fluid circulating through the loop reactor system comprises a continuous phase comprising the ionic liquid and a dispersed phase comprising hydrocarbons.

2. The process of claim 1, wherein the organic cation of the ionic liquid comprises an ammonium cation, a pyrrolidinium cation, a pyridinium cation, an imidazolium, a phosphonium cation, or a combination thereof.

3. The process of claim 1, wherein the halometallate anion comprises a metal selected from Al, Ga, In, Mn, Fe, Co, Ni, Cu, Zn, or a combination thereof, and a halide selected from F, Cl, Br, I, or a combination thereof.

4. The process of claim 1, wherein the halometellate anion is a haloaluminate anion.

5. The process of claim 1, wherein the ionic liquid is present in an amount of from 35 vol. % to 75 vol. % of a total volume of fluid in the loop reactor.

6. The process of claim 1, wherein the process has a selectivity for C6 of at least 70%, and the alkylate has a mole ratio of dimethylbutane to methylpentane of greater of at least 10.

7. The process of claim 1, further comprising introducing a co-catalyst to the loop reactor.

8. The process of claim 7, wherein the co-catalyst comprises a Brøonsted acid selected from the group consisting of HCl, HBr, HI, and mixtures thereof, or a Brøonsted acid precursor.

9. The process of claim 1, wherein a conversion of the bio-ethylene is at least 95%.

10. The process of claim 1, wherein the alkylate has a RON of 94 or more, or 95 or more, or 96 or more, or 97 or more, or 98 or more, or 99 or more, or 100 or more.

11. The process of claim 1, wherein the temperature is in a range of from 35° C. to 70° C.

12. The process of claim 1, wherein the pressure is in a range of from 350 psig to 500 psig (2413 kPa to 3447 kPa).

13. The alkylation process of claim 1 further comprising:
 diverting a portion of fluid circulating through the loop reactor to separator, wherein the fluid comprises an ionic liquid phase and a hydrocarbon phase comprising alkylate and unreacted isobutane; and
 separating the hydrocarbon phase into an alkylate stream and an unreacted isobutane stream; and
 recycling at least one of the unreacted isobutane stream and the ionic liquid stream.

14. The process of claim 13, further comprising:
 regenerating at least a portion of the ionic liquid in the ionic liquid phase; and
 recycling the regenerated ionic liquid catalyst to the loop reactor.

15. The process of claim 1, wherein the bio-ethylene feed is obtained by dehydration of an ethanol feed derived from fermentation or other microbial production processes.

\* \* \* \* \*